US009668743B2

(12) United States Patent
Cully et al.

(10) Patent No.: US 9,668,743 B2
(45) Date of Patent: Jun. 6, 2017

(54) SINGLE ACCESS FLOW-REVERSAL CATHETER DEVICES AND METHODS

(71) Applicant: W. L. Gore & Associates, Inc., Newark, DE (US)

(72) Inventors: Edward H. Cully, Flagstaff, AZ (US); Benjamin M. Trapp, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 162 days.

(21) Appl. No.: 14/747,680

(22) Filed: Jun. 23, 2015

(65) Prior Publication Data
US 2015/0289880 A1 Oct. 15, 2015

Related U.S. Application Data

(62) Division of application No. 13/803,423, filed on Mar. 14, 2013, now Pat. No. 9,084,857.
(Continued)

(51) Int. Cl.
*A61M 25/10* (2013.01)
*A61M 1/00* (2006.01)
(Continued)

(52) U.S. Cl.
CPC .. *A61B 17/12118* (2013.01); *A61B 17/12036* (2013.01); *A61B 17/12045* (2013.01); *A61B 17/12109* (2013.01); *A61B 17/12113* (2013.01); *A61B 17/12136* (2013.01); *A61B 17/12168* (2013.01); *A61B 17/22* (2013.01);
(Continued)

(58) Field of Classification Search
CPC ........ A61B 17/12036; A61B 17/12045; A61B 17/12109; A61B 17/12113; A61B 17/12118; A61B 17/12136; A61B 17/12168; A61B 17/22; A61B 2017/00986; A61B 2017/22079; A61B 2217/005; A61B 2017/22067; A61B 2017/12127; A61B 2017/22055; A61F 2/01; A61F 2/013; A61F 2002/011; A61M 1/34; A61M 1/3621; A61M 2025/1013; A61M 2025/1097;
(Continued)

(56) References Cited

U.S. PATENT DOCUMENTS 4,490,421 A 12/1984 Levy
4,573,966 A 3/1986 Weikl et al.
(Continued)

FOREIGN PATENT DOCUMENTS

EP 0427429 A2 10/1990
EP 0682952 A 11/1995
(Continued)

OTHER PUBLICATIONS

International Search Report for PCT/US2013/033798 mailed Jul. 24, 2013 corresponding to U.S. Appl. No. 13/803,423.

*Primary Examiner* — Adam Marcetich

(57) ABSTRACT

Embodiments herein include devices and methods directed toward creating reverse flow within a vessel and thereby providing protection against embolic debris. Embodiments comprise a catheter and a plurality of occluders that are expandable and adjustable within a lumen to create low-pressure areas that reroute blood flow and embolic debris therein.

8 Claims, 15 Drawing Sheets

Related U.S. Application Data

(60) Provisional application No. 61/624,973, filed on Apr. 16, 2012.

(51) Int. Cl.

| | | |
|---|---|---|
| *A61B 17/12* | (2006.01) | |
| *A61M 1/36* | (2006.01) | |
| *A61M 1/34* | (2006.01) | |
| *A61F 2/01* | (2006.01) | |
| *A61B 17/00* | (2006.01) | |
| *A61B 17/22* | (2006.01) | |

(52) U.S. Cl.
CPC ............... *A61F 2/01* (2013.01); *A61F 2/013* (2013.01); *A61M 1/34* (2013.01); *A61M 1/3621* (2013.01); *A61M 25/1011* (2013.01); *A61B 2017/00986* (2013.01); *A61B 2017/22079* (2013.01); *A61B 2217/005* (2013.01); *A61F 2002/011* (2013.01); *A61M 2025/1015* (2013.01)

(58) Field of Classification Search
CPC .......... A61M 1/3613; A61M 2210/127; A61M 1/3659
See application file for complete search history.

(56) References Cited

U.S. PATENT DOCUMENTS

| | | |
|---|---|---|
| RE32,983 E | 7/1989 | Levy |
| 4,906,244 A | 3/1990 | Pinchuk et al. |
| RE33,561 E | 3/1991 | Levy |
| 5,106,363 A * | 4/1992 | Nobuyoshi ......... A61M 25/104 604/523 |
| 5,330,428 A | 7/1994 | Wang et al. |
| 5,348,538 A | 9/1994 | Wang et al. |
| 5,403,340 A | 4/1995 | Wang et al. |
| 5,447,497 A | 9/1995 | Sogard et al. |
| 5,484,412 A | 1/1996 | Pierpont |
| 5,500,181 A | 3/1996 | Wang et al. |
| 5,556,383 A | 9/1996 | Wang et al. |
| 5,765,568 A | 6/1998 | Sweezer et al. |
| 5,830,182 A | 11/1998 | Wang et al. |
| 5,951,941 A | 9/1999 | Wang et al. |
| 6,146,356 A | 11/2000 | Wang et al. |
| 6,171,278 B1 | 1/2001 | Wang et al. |
| 6,284,333 B1 | 9/2001 | Wang et al. |
| 6,406,457 B1 | 6/2002 | Wang et al. |
| 7,048,713 B2 | 5/2006 | Wang |
| 7,998,104 B2 | 8/2011 | Chang |
| 8,002,728 B2 | 8/2011 | Chang |
| 8,157,760 B2 | 4/2012 | Criado et al. |
| 8,343,089 B2 | 1/2013 | Chang |
| 2002/0173815 A1 | 11/2002 | Hogendijk et al. |
| 2003/0050662 A1 | 3/2003 | Don |
| 2003/0109916 A1 * | 6/2003 | Don Michael ......... A61F 2/013 623/1.11 |
| 2004/0019310 A1 | 1/2004 | Hogendijk |
| 2005/0228432 A1 | 10/2005 | Hogendijk et al. |
| 2007/0021774 A1 | 1/2007 | Hogendijk |
| 2008/0132937 A1 | 6/2008 | Hartley et al. |
| 2009/0024072 A1 | 1/2009 | Criado et al. |
| 2009/0198172 A1 | 8/2009 | Garrison et al. |
| 2009/0254166 A1 | 10/2009 | Chou et al. |
| 2010/0191170 A1 | 7/2010 | Chang |
| 2010/0204684 A1 | 8/2010 | Garrison et al. |
| 2010/0217276 A1 | 8/2010 | Garrison et al. |
| 2010/0280431 A1 | 11/2010 | Criado et al. |
| 2011/0004147 A1 | 1/2011 | Renati et al. |
| 2011/0034986 A1 | 2/2011 | Chou et al. |
| 2011/0082408 A1 | 4/2011 | Chang |
| 2011/0087147 A1 | 4/2011 | Garrison et al. |
| 2011/0166496 A1 | 7/2011 | Criado et al. |
| 2011/0166497 A1 | 7/2011 | Criado et al. |
| 2011/0301571 A1 * | 12/2011 | Guimaraes ......... A61M 25/0662 604/509 |

FOREIGN PATENT DOCUMENTS

| | | |
|---|---|---|
| EP | 0 839 550 | 5/1998 |
| WO | 9532745 A1 | 12/1995 |
| WO | 00/51675 | 9/2000 |
| WO | 2000076390 A | 12/2000 |
| WO | 2012/021406 | 2/2012 |

\* cited by examiner

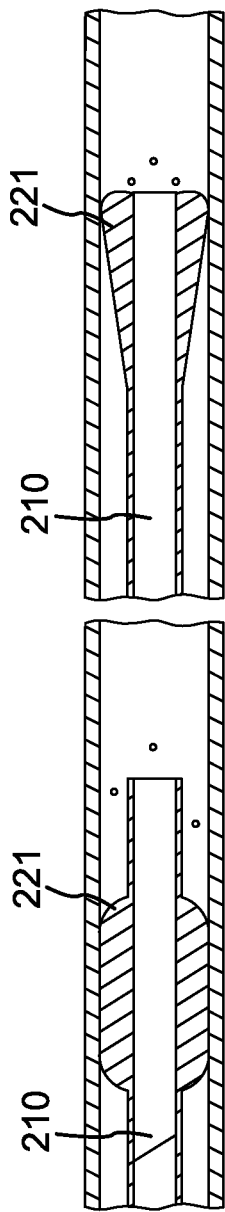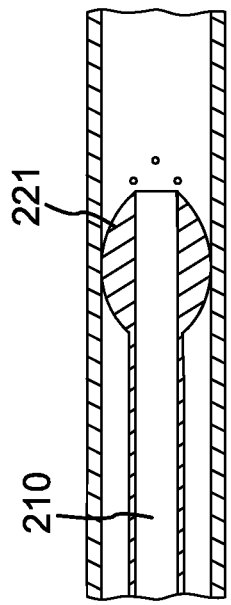

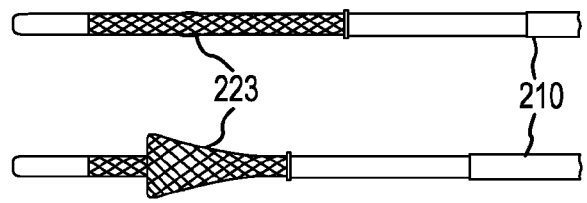
FIG. 10
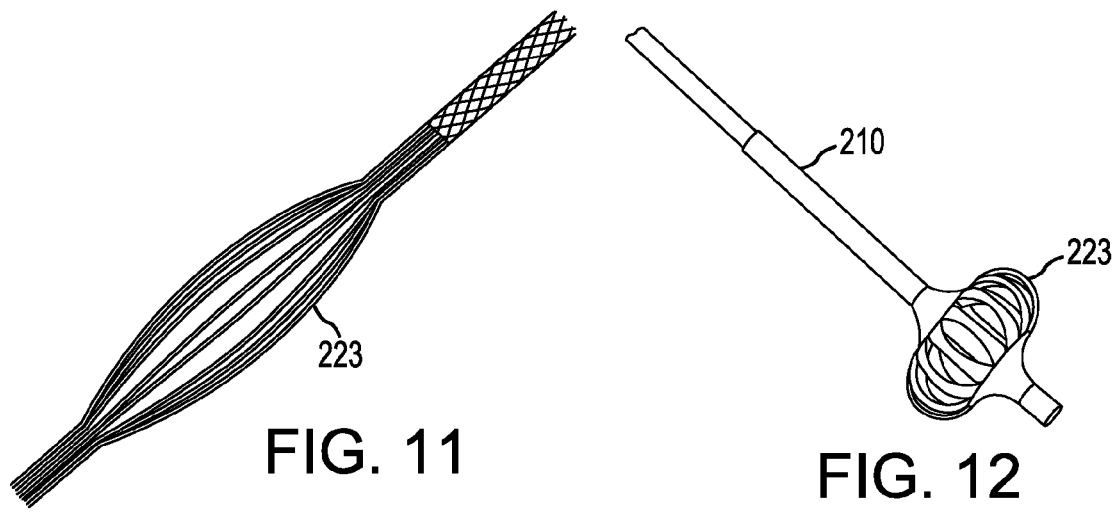
FIG. 11
FIG. 12
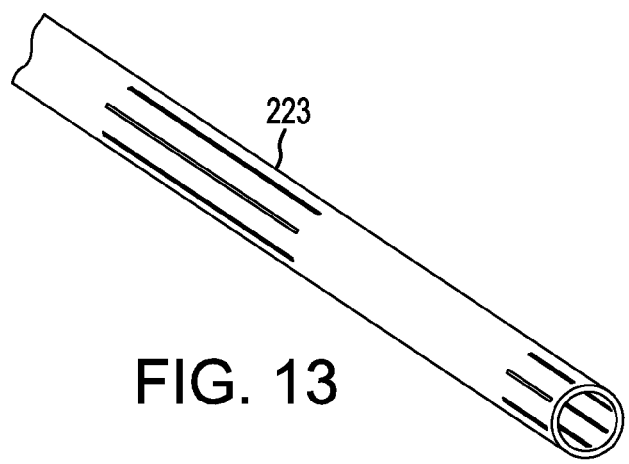
FIG. 13

SINGLE ACCESS FLOW-REVERSAL CATHETER DEVICES AND METHODS

BACKGROUND OF THE INVENTION

Field of the Invention

The present disclosure relates generally to catheter devices and methods for protecting against embolic debris during vascular interventions. More particularly, the devices and methods described herein can be used with endovascular procedures in a mammalian body and achieve blood flow-reversal within the arterial vasculature as well as blood return without a venous return.

Discussion of the Related Art

Contralateral flow occurs when there are arterial vessels that are in fluid communication at two points, e.g. a proximal and distal location. When the fluid pressure in one arterial conduit drops, the pressure from the other arterial conduit can cause the blood from the other side to flow into this conduit. For example, the arterial side of the cerebral circulatory system generally can be seen as divided into two sets of contralateral arteries, both sets originating from the aortic arch with one set feeding the left side of the brain and the other set feeding the right side. A large number of minor and major communicating vessels connect these contralateral arteries. As such, if the blood pressure becomes low enough on a given side, the pressure on the contralateral is sufficient to cause blood to flow across the communicating vessels and in a retrograde fashion towards the low-pressure source. Artificially and temporarily occluding the natural antegrade flow in a cerebral vessel and providing a low-pressure outlet for the blood can induce this retrograde effect.

This effect can be particularly useful when treating an artery in or near the cerebral vasculature, or in another vessel with similar contralateral flow properties. Endovascular treatment of a blood vessel, which has a reduced diameter, for example, through the effects of lesions called atheroma or the occurrence of cancerous tumors, can generate free-floating debris. Such debris may cause damaging embolisms, and embolisms occurring in the brain are particularly dangerous. By inducing retrograde flow across a lesion in a cerebral vessel, any debris generated can be routed away from the brain.

Current devices that create reverse flow may be improved upon in a variety of respects. For example, some devices require withdrawal of the patient's blood to create retrograde flow across a lesion, and the patient's blood during this process is not conserved. Furthermore, current devices may not maintain continuous reverse flow but rather intermittent reverse flow. Maintaining a continuous reverse flow rather than an intermittent reverse flow further minimizes the risk that embolic debris will migrate toward the brain. Another current device does conserve blood and does maintain constant flow. However, this device requires multiple access sites within a patient's vasculature, which presents more risk to the patient and impacts ease of use for the clinician. Therefore, there is a need for endovascular devices and methods that create reverse flow and protect against embolic debris while conserving the patient's blood and requiring only a single vascular access site.

SUMMARY OF THE INVENTION

Described embodiments are directed toward endovascular devices and methods to reverse blood flow, continuous or discontinuous, across a treatment site (e.g., lesion) and reroute blood within the vasculature using only a single vasculature access site.

According to one embodiment, a flow-reversal catheter device comprises a catheter, a first occluder at or near a distal end of the catheter, a return port located proximally to the first occluder, a conduit connecting a distal opening of the catheter to the return port, and a mechanism configured to create a continuous pressure gradient so that blood flows into the distal opening of the catheter, through the conduit, and exits through the return port. Such mechanisms can include a second occluder positioned proximal to the first occluder, an external pump, and/or a drain container.

According to another embodiment, a method for reversing blood flow in a vessel, such as an artery supplying blood to the brain, utilizing a flow-reversal catheter device is provided. Yet another embodiment comprises a method for treatment of a cerebral vessel having a stenosis utilizing the flow-reversal catheter device.

BRIEF DESCRIPTION OF THE DRAWINGS

The accompanying drawings are included to provide a further understanding of the present disclosure and are incorporated in and constitute a part of this specification, illustrate various embodiments, and together with the description serve to explain the principles of the disclosure.

FIGS. 2-4 illustrate a side view of various inflatable occluders;

FIGS. 10-13 illustrate a side view of various slide-actuated occluders;

DETAILED DESCRIPTION OF THE ILLUSTRATED EMBODIMENTS

Figure 1:
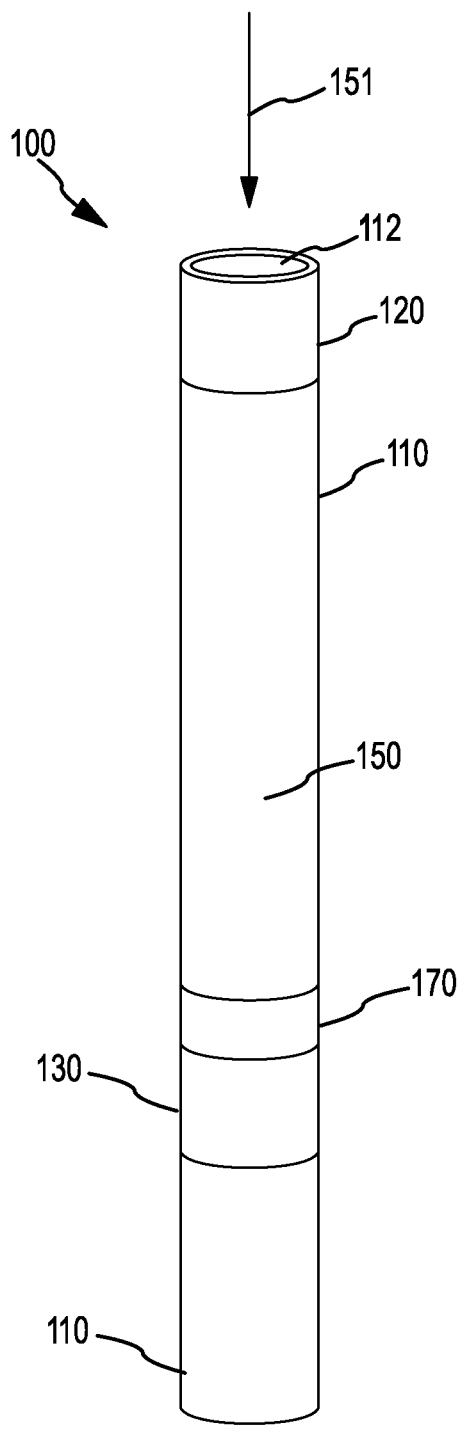
FIG. 1 illustrates schematic views of a flow-reversal catheter device.
Figure 5:
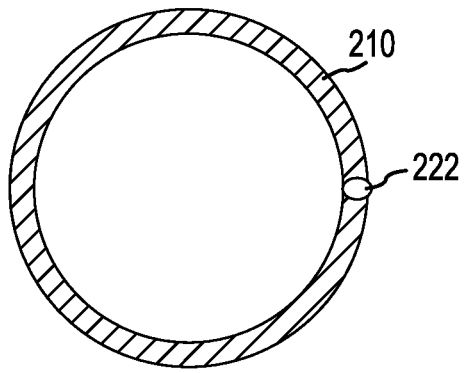
FIGS. 5-9 illustrate a cross-sectional view of inflation lumen configurations.
Figure 6:
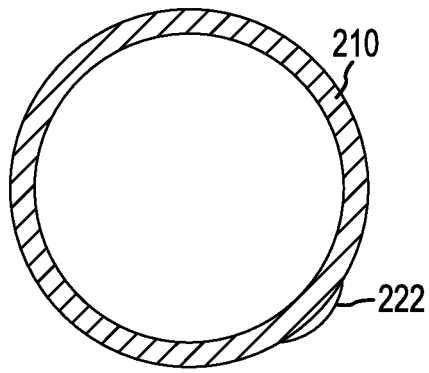
Figure 7:
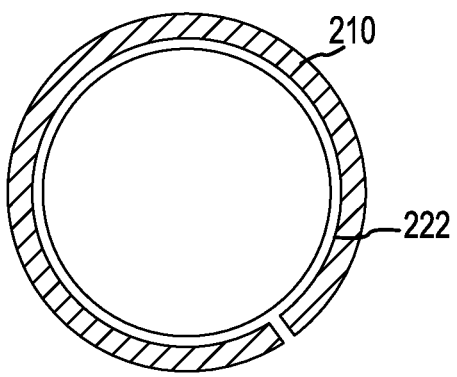
Figure 8:
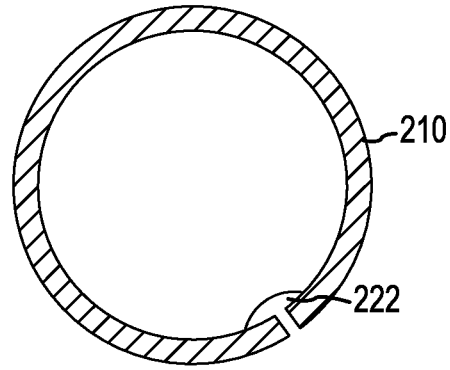
Figure 9:
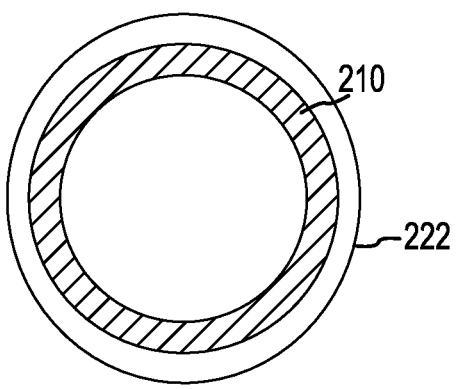

Persons skilled in the art will readily appreciate that various embodiments may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various embodiments, and in that regard, the drawing figures should not be construed as limiting. Although embodiments may be described in connection with various principles and beliefs, the present disclosure should not be bound by theory.

The terms "downstream" or "antegrade" and "upstream" or "retrograde," when used herein in relation to the patient's vasculature, refer respectively, to the direction of blood flow and the direction opposite that of blood flow, respectively. In the arterial system, "downstream" or "antegrade" refers to the direction further from the heart, while "upstream" or "retrograde" refers to the direction closer to the heart. The terms "proximal" and "distal," when used herein in relation to a device or device component refer to directions closer to and farther away from the operator of the device. Since the present disclosure is not limited to peripheral or central approaches, the device should not be narrowly construed when using the terms proximal or distal since device features may be slightly altered relative to the anatomical features and the device position relative thereto.

Described embodiments are directed toward endovascular devices and methods to reverse blood flow, continuous or discontinuous, across a treatment site (e.g., lesion) and reroute blood within the vasculature using only a single vasculature access site. Embodiments herein are directed toward rerouting embolic debris of a wide range of particle sizes away from particularly at-risk areas, such as the cerebrovascular system, during an endovascular treatment, and can further be configured to filter embolic debris. These embodiments are configured to traverse tortuous vessel anatomy, establish reverse flow across a treatment site, and provide a working lumen through which a clinician can deliver one or more secondary endovascular devices.

As used herein, "embolic debris" means any biologic or non-biologic mass, the presence of which in the vasculature presents a risk, including, but not limited to, plaque, emboli, etc.

"Reverse flow," as used herein, is the flow of blood opposite to the direction of blood flow under normal blood flow conditions. Flow-reversal is achieved by creating a pressure gradient so blood flow is reversed and directed from the treatment site into lumen of catheter to be rerouted to another location. The pressure gradient can be facilitated by creating a low-pressure source(s), which can be within the catheter device itself or created in a desired location within the vasculature that is in fluid communication with the conduit of the catheter device.

As mentioned previously, a purpose of reverse flow is to channel embolic debris of a wide range of particle sizes away from particularly at-risk areas during an endovascular treatment. In accordance with an embodiment, blood, along with embolic debris in some embodiments, from the treatment site is rerouted through the catheter to another location along the delivery path. "Delivery path," as used herein, is the path of an endovascular device through the vasculature from an entry point to a treatment site. Along this path from high to low pressure, a filter can be included to capture embolic debris from the blood.

A flow-reversal catheter device comprises: (i) a catheter having proximal and distal ends with a lumen extending therethrough; (ii) a first occluder at the distal end of catheter; (iii) a return port located proximally to first occluder; (iv) a conduit fluidly connecting a distal opening of catheter to return port; and (v) a mechanism (not shown) configured to create a pressure gradient so that blood flows into distal opening, through conduit, and exits through return port. In one embodiment, with reference to schematic FIG. 1, intended to show relative positioning of the elements, a flow reversal catheter 100 comprises (i) a catheter 110 having proximal and distal ends with a lumen extending therethrough; (ii) a first occluder 120 at the distal end of catheter 110; (iii) a return port 130 located proximally to first occluder 120; (iv) a conduit 150 fluidly connecting a distal opening 112 of catheter 110 to return port 130; and (v) a second occluder 170 that is proximal the first occluder 120 and distal the return port 130.

In various embodiments, flow-reversal catheter device 100 is configured such that a single site entry is all that is required to reroute blood, along with filtering and/or rerouting embolic debris. In other words, only a single pass of a medical device, namely flow-reversal catheter device 100, through the wall of access vessel is required. No other entry point is required to reroute blood flowing into conduit to another location within the vasculature. In the case of an arterial side procedure, blood is rerouted to a location within the arterial side and access to the venous side, i.e., a venous return, is not employed. As such, return port 130 is locatable, during use of catheter device 100, at a point along the vasculature delivery path.

Catheter 110 is generally any elongated structure configured to provide a working lumen through which blood and embolic debris can be channeled and/or through which one or more secondary endovascular devices (e.g., a balloon catheter, balloon wire, delivery catheter, drug delivery device, filters, stents, stent-grafts, diagnostic catheters, infusion catheters, aspiration catheters, or any other device configured to be delivered and/or deployed through catheter 110) can be delivered through lumen of catheter 110. A catheter 110 comprises a proximal opening and a distal opening and comprises at least one lumen extending therethrough. A proximal opening of catheter can connect to a catheter hub.

Catheter 110 can be configured to be bendable to traverse through tortuous vasculature, and can further be configured to minimize or eliminate kinking. Catheter 110 can comprise an inner diameter of sufficient size to permit passage of blood flow, a secondary endovascular device, and optionally a third occluder described below. Catheter 110 can comprise an outer diameter of sufficient size to permit passage through vasculature to access a treatment site. Catheter 110 can comprise any medical-grade material. Catheter 110 can comprise polymeric or metallic materials or combinations thereof. For example, catheter 110 can comprise a polymeric film tube with spiral or braided nitinol reinforcements.

Typical materials used to construct catheter 110 can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenylene Ether (PPE), Modified Polyphenylene Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluoroethylene (ECTFE), Ethylene, Ethylene Tetrafluoroethylene (ETFE), Polychlortrifluoroethylene (PCTFE), Polytetrafluoroethylene (PTFE), expanded Polytetrafluoroethylene (ePTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

In various embodiments, first occluder 120 comprises any radially expandable and collapsible structure at the distal end of catheter 110 and configured, when in an expanded state, to substantially block or partially constrict the flow of blood about the periphery of catheter 110 and thereby channel blood and emboli into distal opening 112. First occluder 120 is delivered in a collapsed configuration and then expanded to block or constrict the flow of blood proximate a treatment site.

Blocking the flow of blood facilitates the reversal of blood flow across a treatment site. By way of example, expanding first occluder 120 in the common carotid artery blocks the flow through the common carotid artery and causes the pressure on the downstream side, i.e., distal side of first occluder 120, to drop, thereby facilitating blood from contralateral vessels to flow toward the lower pressure and flow into conduit 150 hence sweeping embolic debris into distal opening 112 of catheter 110. Contralateral flow, once stabilized, maintains the blood pressure on the downstream side flowing into distal opening 112 at about 70 mmHg to about 90 mmHg.

First occluder 120 can be any shape which occludes a radial space about the distal region or end of catheter 110, so as to ensure blood and emboli is directed into distal opening 112 of catheter 110 rather than becoming trapped between the intraluminal wall of the vessel and the outer wall of catheter 110. For example, first occluder 120 can be disc-shaped, donut-shaped, cylindrical, cone-shaped (e.g., pear-shaped), funnel-shaped, or any other shape that substantially occludes the flow of blood about the radial space of the distal region of catheter 110 and define the outer wall of catheter 110 to permit blood to pass through the distal opening 112 of catheter 110.

First occluder 120 can transition between a collapsed configuration and an expanded configuration in any manner. For example, first occluder 120 can be inflated, deflated, self-expanding, and/or slideably actuated.

With reference to FIGS. 2-9, a first occluder can comprise an inflatable occluder 221, such as a balloon. Inflatable occluder 221 obtains its expanded configuration by passing a fluid through an inflation lumen 222, and its collapsed configuration by withdrawing the fluid from inflatable occluder 221 through inflation lumen 222. Inflation lumen 222 can be embedded within or longitudinally extending alongside the wall of catheter 210, or between the wall of catheter 210 and a coaxial outer sheath or a secondary catheter. Cross-sectional views of various configurations of inflation lumen 222 are illustrated in FIGS. 5-9.

Inflatable occluder 221 formation can be carried out in any conventional manner using known extrusion, injection molding and other molding techniques. Typically, there are three major steps in the process that include extruding a tubular pre-form, molding inflatable occluder 221 and annealing inflatable occluder 221. Depending on the method of manufacturing inflatable occluder 221, the pre-form can be axially stretched before it is blown. Techniques for inflatable occluder 221 formation are described in U.S. Pat. No. 4,490,421 to Levy; RE32,983 to Levy; RE33,561 to Levy; and U.S. Pat. No. 5,348,538 to Wang et al., all of which are hereby incorporated by reference.

Inflatable occluder 221 can be formed from using any materials known to those of skill in the art. Commonly employed materials include the thermoplastic elastomeric and non-elastomeric polymers and the thermosets including the moisture curable polymers. Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See U.S. Pat. No. 5,500,181 to Wang et al., for example, which is hereby incorporated by reference. As used herein, the term "copolymer" shall be used to refer to any polymer formed from two or more monomers, e.g., 2, 3, 4, 5, etc.

Useful polyamides include, but are not limited to, nylon 12, nylon 11, nylon 9, nylon 6/9 and nylon 6/6. The use of such materials is described in U.S. Pat. No. 4,906,244 to Pinchuk et al., for example, which is hereby incorporated by reference.

Examples of some copolymers of such materials include the polyether-block-amides, available from Elf Atochem North America in Philadelphia, Pa. under the trade name of PEBAX®. Another suitable copolymer is a polyetheresteramide.

Suitable polyester copolymers include, for example, polyethylene terephthalate and polybutylene terephthalate, polyester ethers and polyester elastomer copolymers such as those available from DuPont in Wilmington, Del. under the trade name of HYTREL®.

Block copolymer elastomers such as those copolymers having styrene end blocks, and midblocks formed from butadiene, isoprene, ethylene/butylene, ethylene/propene, and so forth can be employed herein. Other styrenic block copolymers include acrylonitrile-styrene and acrylonitrile-butadiene-styrene block copolymers. Also, block copolymer thermoplastic elastomers in which the block copolymer is made up of hard segments of a polyester or polyamide and soft segments of polyether can be employed herein.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials that can be employed in inflatable occluder 221 formation are further described in, for example, U.S. Pat. No. 6,406,457 to Wang et al.; U.S. Pat. No. 6,284,333 to Wang et al.; U.S. Pat. No. 6,171,278 to Wang et al.; U.S. Pat. No. 6,146,356 to Wang et al.; U.S. Pat. No. 5,951,941 to Wang et al.; U.S. Pat. No. 5,830,182 to Wang et al.; U.S. Pat. No. 5,556,383 to Wang et al.; U.S. Pat. No. 5,447,497 to Sogard et al.; U.S. Pat. No. 5,403,340 to Wang et al.; U.S. Pat. No. 5,348,538 to Wang et al.; and U.S. Pat. No. 5,330,428 to Wang et al., all of which are hereby incorporated by reference.

The above materials are intended for illustrative purposes only, and not as a limitation on the scope of the present disclosure. Suitable polymeric materials available for use are vast and too numerous to be listed herein and are known to those of ordinary skill in the art.

With reference to FIGS. 10-13, a first occluder can comprise a slide-actuated occluder 223, such as an expandable mesh, braided, or ribbed (e.g., malecot-type) structure which radially expands upon application of a longitudinal compression force and collapses upon application of a longitudinal tension force. Slide-actuated occluder 223 can be attached at or near the distal end of catheter 210 and attached to an actuating member (e.g., outer tube or semi-rigid longitudinal connector) on its proximal end, or vice versa, wherein the actuating member is slidably coupled to catheter 210. Slide-actuated occluder 223 can comprise any medical grade material, such as a polymeric or metallic material.

Slide-actuated occluder 223 can comprise a covering, such as an elastomeric polymer film, to block or constrict blood flow. The covering can be elastic so that it stretches as the space between the braided filaments or ribs separates during radial expansion. Alternatively, a tightly knit mesh or the like with or without a covering can block or constrict blood flow.

Referring back to FIG. 1, first occluder 120 can be attached to catheter 110 by various bonding techniques. Examples include, but are not limited to, solvent bonding, thermal adhesive bonding and heat shrinking or sealing. The selection of the bonding technique is dependent upon the materials from which the occluder and catheter are prepared. For example, U.S. Pat. No. 7,048,713 to Wang, which is hereby incorporated by reference, provides for general teachings relating to the bonding of an inflatable occluder to a catheter. Such modes of catheter attachment can be similarly applied to the second occluder and third occluder described below.

Figure 14:
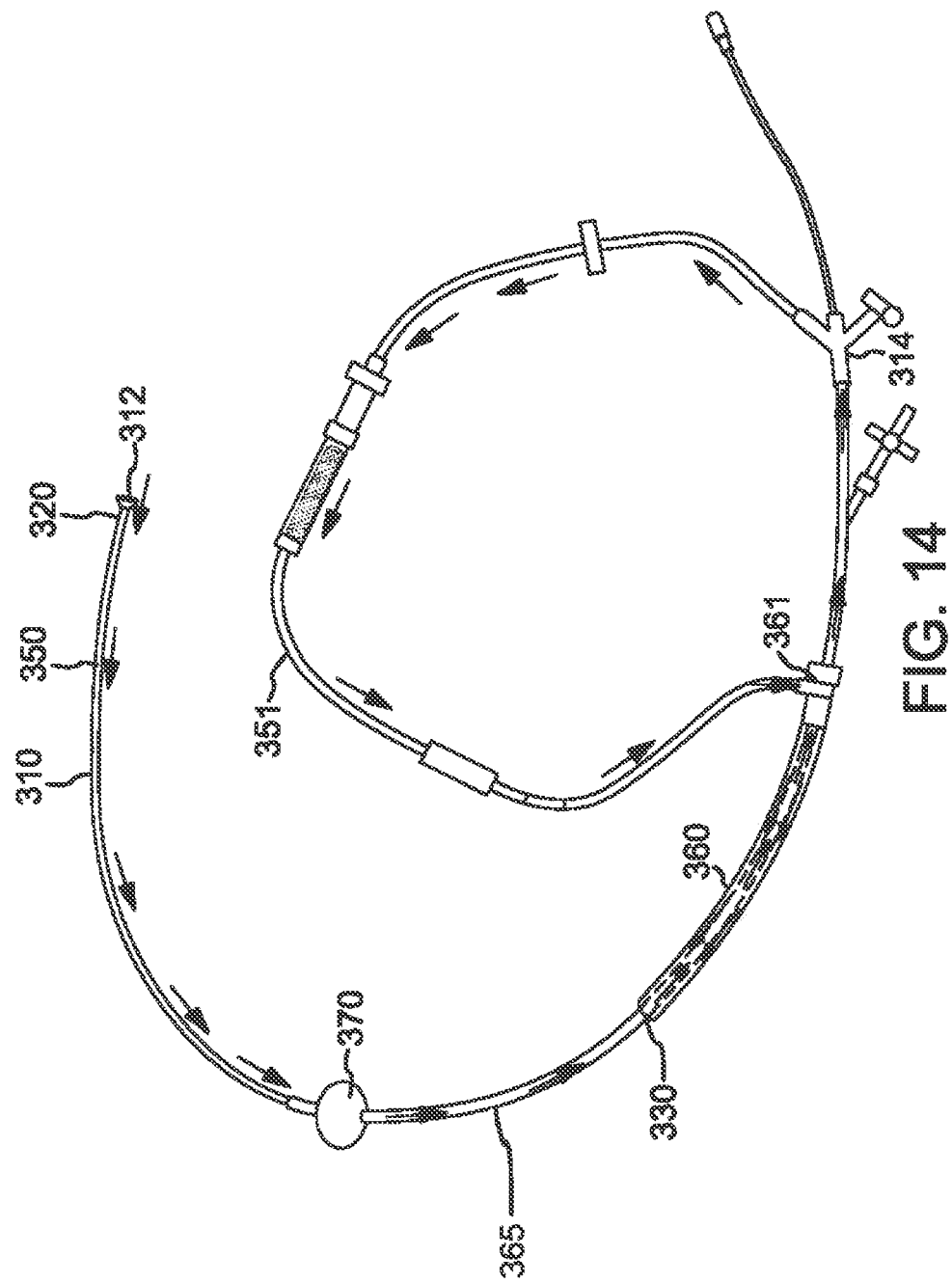
FIG. 14 illustrates a side view of a flow-reversal catheter device comprising a second occluder.
Figure 15:
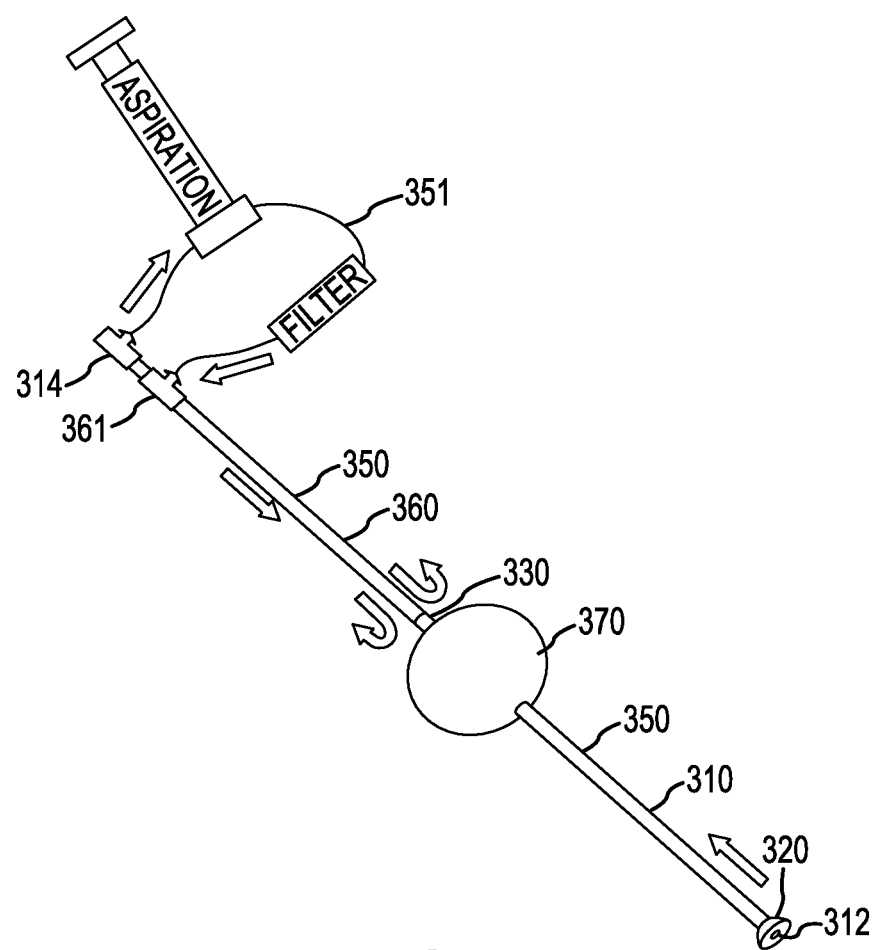
FIG. 15 illustrates a side view of a flow-reversal catheter device comprising a second occluder and an external pump.

With reference to FIGS. 14-15, conduit 350, the path of which is depicted by the arrows in the referenced figures, comprises any structure that provides a blood flow pathway between distal opening 312 of catheter 310 and return port 330. Blood and embolic debris enter conduit 350 at distal opening 312 and flow down the pressure gradient toward return port 330, where blood is reintroduced to a region in the access vessel proximal to first occluder 320 as well as a second occluder 370, if present. As such, conduit 350 comprises at least a portion of catheter 310.

During use, conduit 350 can be fully contained within the vasculature along the delivery path. For example, the entire length of conduit 350 can consist of at least a portion of catheter 310. Alternatively, conduit can extend beyond catheter 310. For example, blood can exit the proximal opening of catheter 310 and enter into additional tubing 351 at catheter hub 314. Blood can reenter the arterial vessel at the introducer sheath hub 561 and pass into the interstitial space between catheter 310 and an introducer sheath 360 to be reintroduced into the vasculature at return port 330.

Additional tubing 351 of conduit 350 can comprise any structure that provides additional lumen to connect catheter 310 to return port 330. For example, conduit 350 can comprise tube(s), coupling(s), valve(s), catheter hub(s), or any other lumen-providing or lumen-connecting structure.

Figure 16:
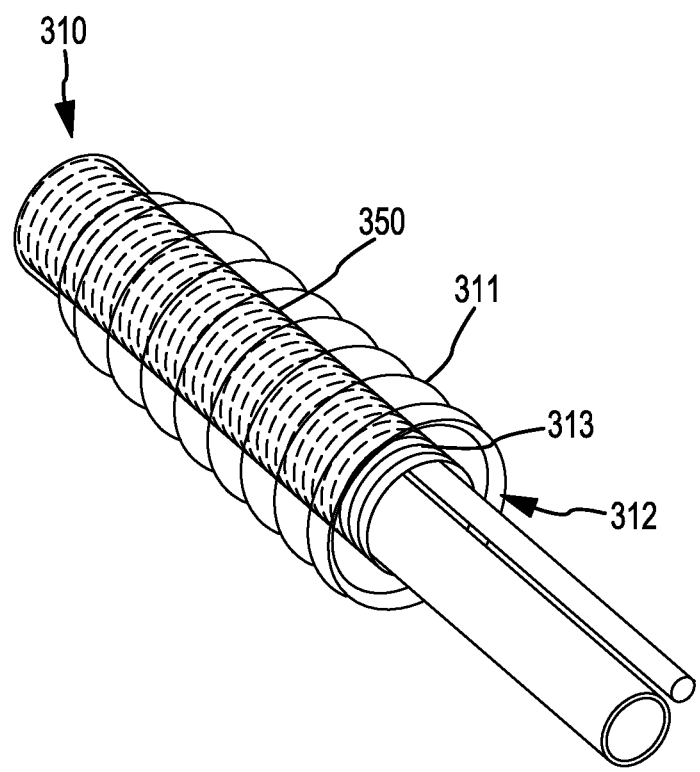
FIG. 16 illustrates a perspective view of a catheter comprising an expandable outer sheath.

With reference to FIG. 16, at least a portion of conduit 350 can be configured to be expandable with an increase in pressure. For example, catheter 310 can be delivered at a first profile and then when blood begins to flow into its lumen, catheter 310 expands with this increase in fluid pressure to a second diameter profile that is greater than the first diameter profile. Catheter 310 can comprise an expandable outer sheath 311 concentric about an inner catheter. In this embodiment, blood will flow between catheter 313 and expandable outer sheath 311, causing outer sheath 311 to expand radially. In addition, a first occluder can be configured to expand catheter 310 to the second profile. In this case, the first occluder would be discontinuous across distal opening 312 of catheter 310 to allow for perfusion of blood.

With reference back to FIG. 14-15, flow-reversal catheter device 100 can further comprise introducer sheath 360. Introducer sheath 360 comprises a distal and proximal end with a lumen therethrough and can be configured to serve as an access port into the vasculature for endovascular devices such as catheter 110 and/or the second occluder catheter. The proximal end of introducer sheath 360 can be coupled to introducer sheath hub 361. Introducer sheath hub 361 can be also coupled to additional tubing 351 to fluidly connect conduit 350 to return port 330.

Figure 17:
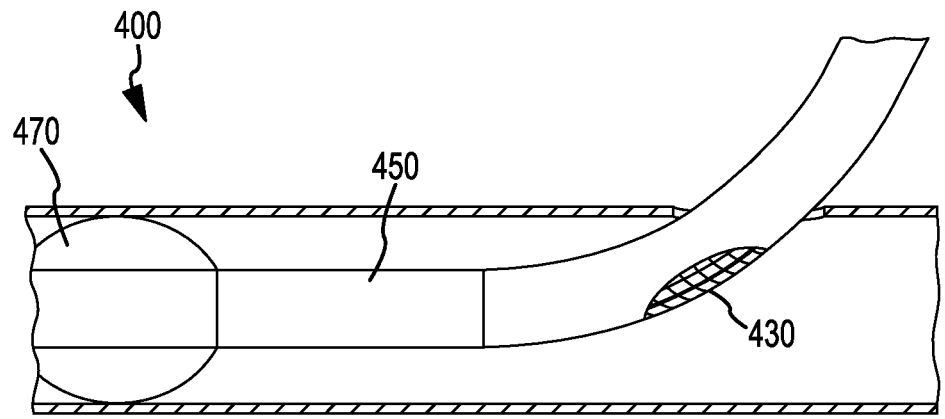
FIGS. 17-18 illustrate side views of various return ports.
Figure 18:
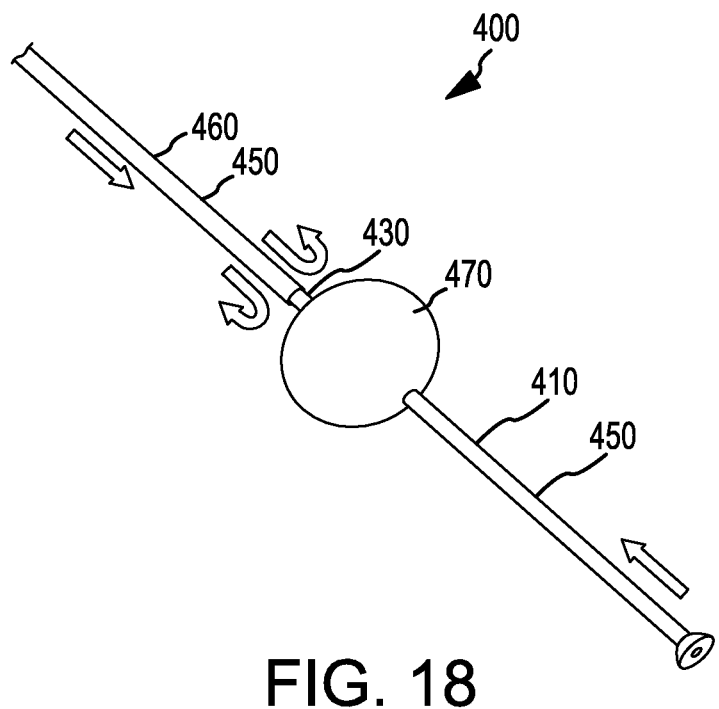

With reference to FIGS. 17-18, return port 430 in various embodiments comprises an opening through which blood exits flow-reversal catheter device 400. During use, return port 430 is locatable within the access vessel proximal to the first occluder (not shown) as well as second occluder 470, if present. For example, return port 430 can comprise an opening in catheter wall (or second occluder catheter wall discussed below), an opening in introducer sheath 460 wall, the distal end or opening of the introducer sheath 460, and/or an opening along any other portion of the conduit 450 along vasculature delivery path proximal the first occluder.

The flow-reversal catheter device further comprises a mechanism to create a pressure gradient, e.g., a low-pressure source that causes blood to flow along the conduit from the distal opening of the catheter to exit out the return port. A mechanism can be configured to provide a continuous pressure gradient, or the pressure gradient can be provided at on-demand, pre-programmed, regular, or intermittent intervals.

Figure 19:
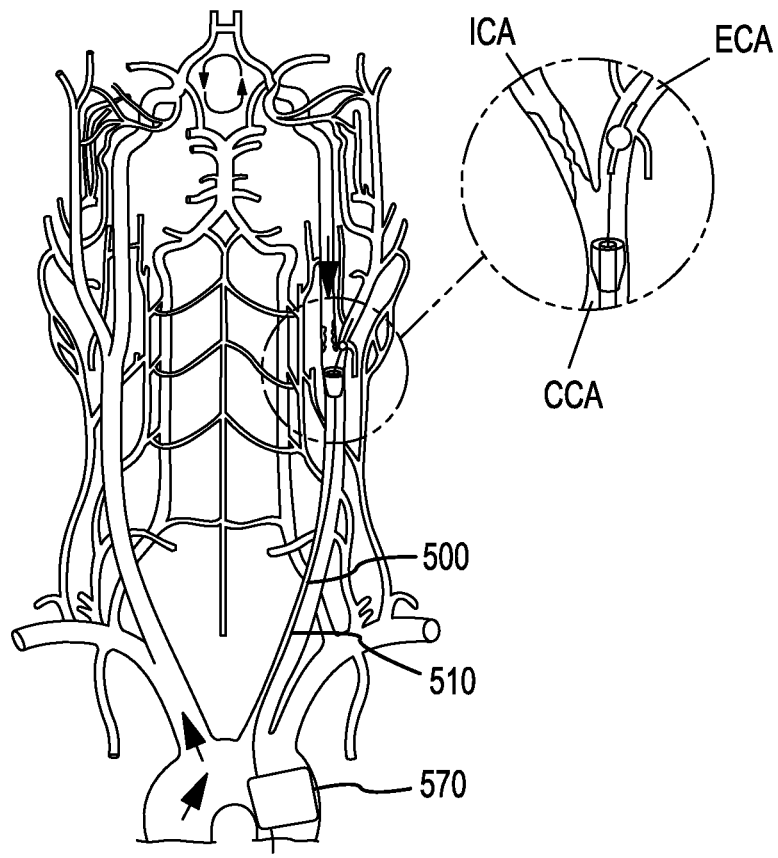
FIGS. 19-20 illustrate side views of a flow-reversal catheter device comprising a second occluder and a side view of the same deployed in the carotid artery.
Figure 20:
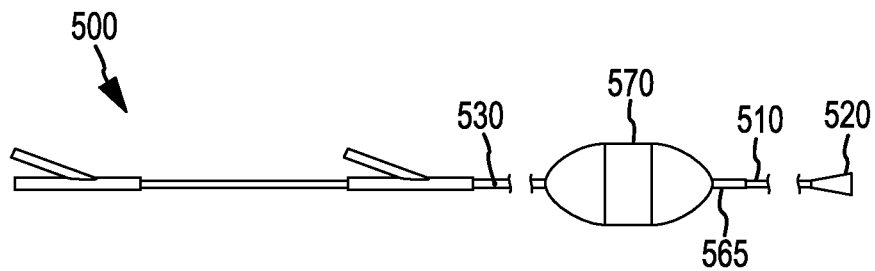

For example, with reference to FIGS. 19-20, this mechanism can comprise a second occluder 570 similarly configured like first occluder 520 to substantially block or partially constrict blood flow and to create a low-pressure source (e.g., less than about 30 mmHg) on the downstream side of second occluder 570. As such, return port 530, during use, is locatable in this downstream-occluded region. In the case of a procedure in the carotid artery or an artery distal thereto, as illustrated in FIG. 19, second occluder 570 can be locatable anywhere along the delivery path (as that term has been defined herein) within or proximal the aortic arch, such as downstream from the left common carotid artery. Constricting downstream of the aortic arch with second occluder 570 in combination with first occluder 520 inflated at the treatment site can increase the pressure of the blood flowing into the common carotid artery opposite the side being treated.

Second occluder 570 can comprise any collapsible and expandable structure of any shape that occludes or constricts a radial space about catheter device 500 and is locatable proximal first occluder 520. In an embodiment, the length of catheter 510 between the first occluder 520 and second occluder 570 can be greater than the distance between the treatment site and a location along delivery path downstream of the left subclavian artery. For example, second occluder 570 can be deployed at a location downstream of the renal arteries or a location downstream of the internal iliac arteries. Second occluder 570 can be coupled to catheter 510, introducer sheath, or a second occluder catheter 565 that slideably fits over catheter 510. Similar to first occluder 520 described above, second occluder 570 can comprise an inflatable occluder or a slide-actuated occluder.

Figure 21:
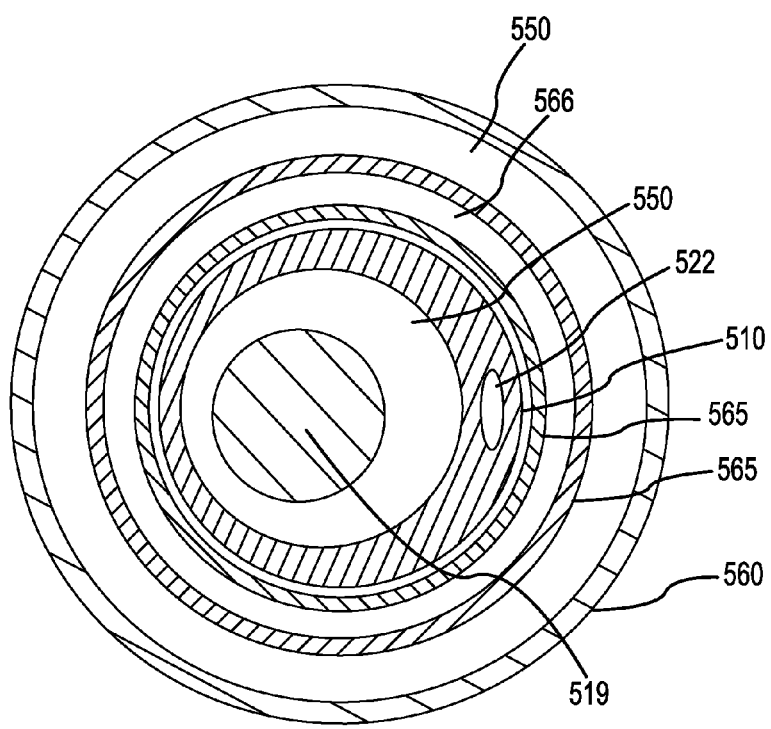
FIG. 21 illustrates a cross-sectional view of a catheter device comprising a first occluder (not shown) coupled to catheter, a second occluder (not shown) coupled to a second occluder catheter, and an introducer sheath.

FIG. 21 illustrates a cross-sectional view of a catheter device 500 comprising a first occluder (not shown) coupled to catheter 510; a second occluder (not shown) coupled to a second occluder catheter 565; and an introducer sheath 560. Catheter 510 comprises an inflation lumen 522 within the wall of catheter 510 and contains a secondary endovascular device 519 within conduit 550. Second occluder catheter 565 comprises an inner and outer tube with an inflation lumen 566 in the intermediate space.

Figure 22:
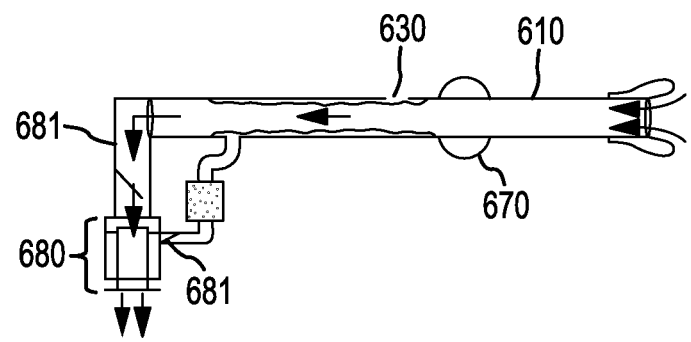
FIGS. 22-23 illustrate side views of a flow-reversal catheter device comprising an external pump.
Figure 23:
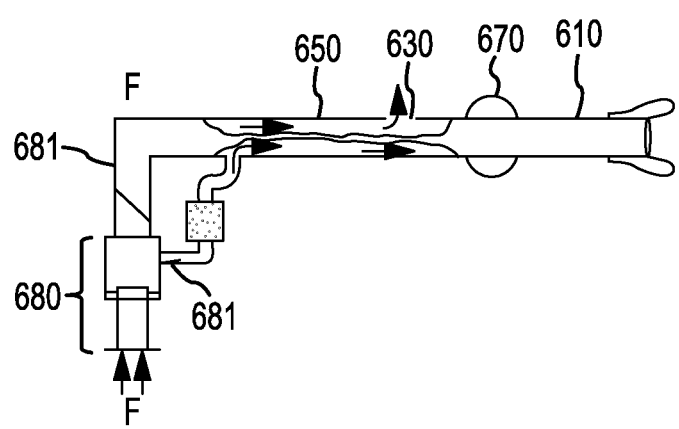

With reference to FIGS. 22-23, another mechanism for creating a pressure gradient along conduit 650 can comprise an external pump 680. For example, external pump 680 can comprise a valved aspirator or syringe connected to conduit 650 and can serve to aspirate blood from catheter 610 to create reverse flow, and then valve(s) 681 are switched to push aspirated blood towards return port 630. Other external pumps 680 can include a motorized pumps, such as a roller pump.

Figure 24:
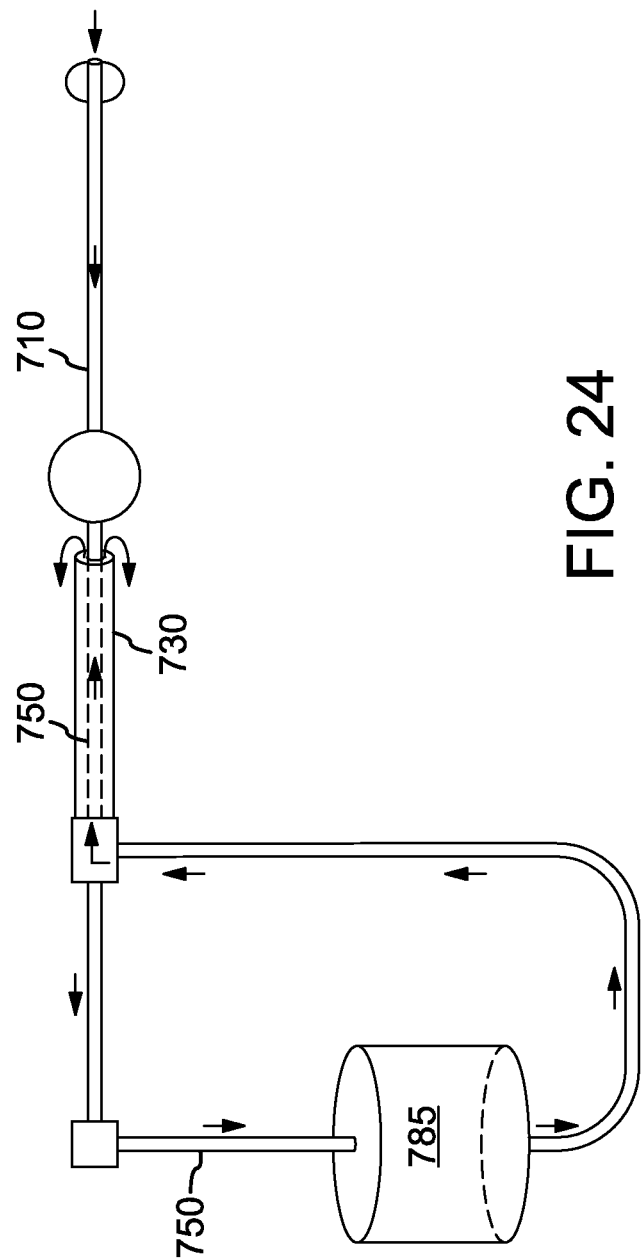
FIG. 24 illustrates a side view of a flow-reversal catheter device comprising a drain container.

With reference to FIG. 24, a mechanism to create a pressure gradient can comprise a drain container 785, such as an IV bag, wherein drain container 785 being at ambient pressure creates reverse flow. In various embodiments, blood flowing into catheter 710 and through conduit 750 will flow into drain container 785. Once the procedure is finished or while the procedure is ongoing, the blood in drain container 785 can be connected to conduit 750 so that blood is returned to the vasculature via return port 730.

Figure 25:
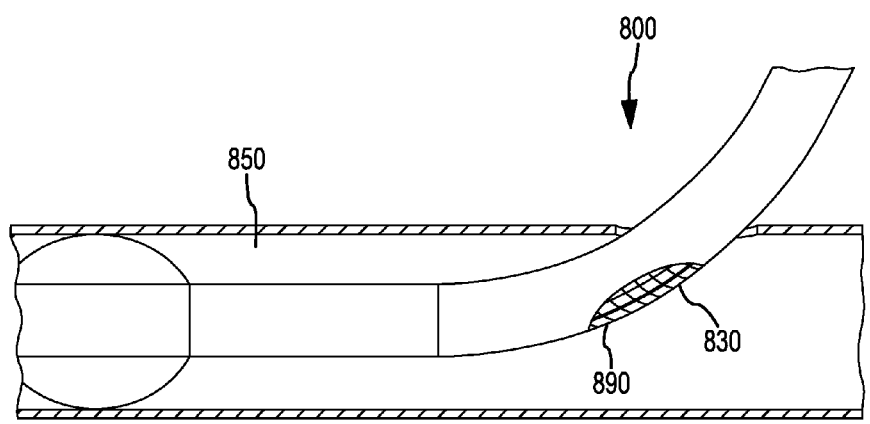
FIGS. 25-26 illustrate a side view of a filter.
Figure 26:
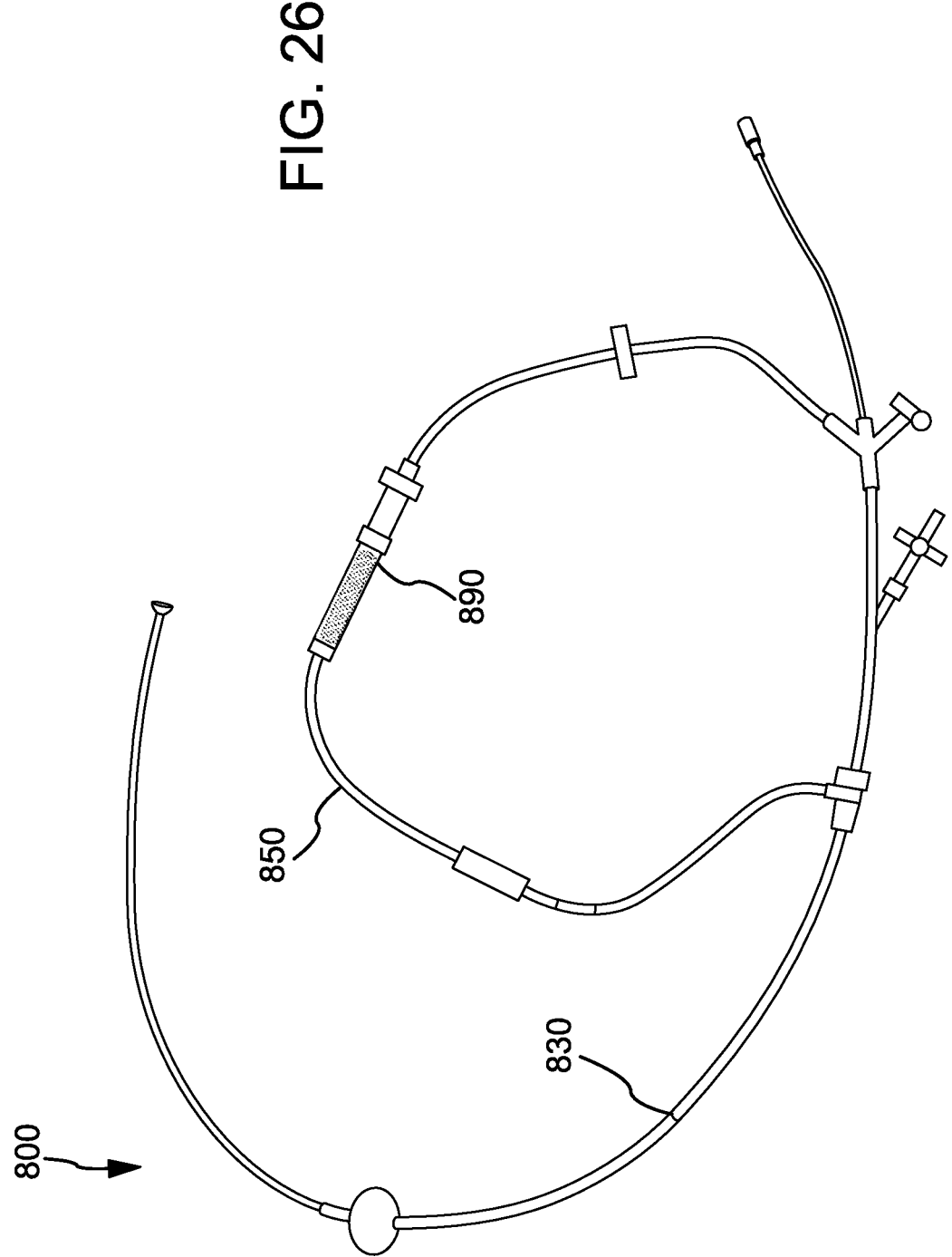

With reference to FIGS. 25-26, catheter device 800 can comprise filter 890. Filter 890 can be locatable in line of conduit 850 or about or across return port 830. Filter 890 comprises any device configured to capture embolic degree, such as embolic debris having a size greater than about 50 µm or greater than about 100 µm. Filter 890 can be configured so that it can be visibly inspected during the procedure. For example, filter can be housed in a transparent or translucent section of conduit 850. In addition, filter 890 can also be configured so that it can be removed, cleaned, or replaced during the procedure, so that the amount of embolic debris can be routinely checked. Various embodiments of filter 890 can comprise a net, mesh basket, screen, or the like.

A flow-reversal catheter device can comprise a single or a plurality of mechanisms to create a pressure gradient along the conduit. For example, a second occluder, an external pump, and a drain container can be combined within a flow-reversal catheter device to create a pressure gradient along the conduit.

Figure 27:
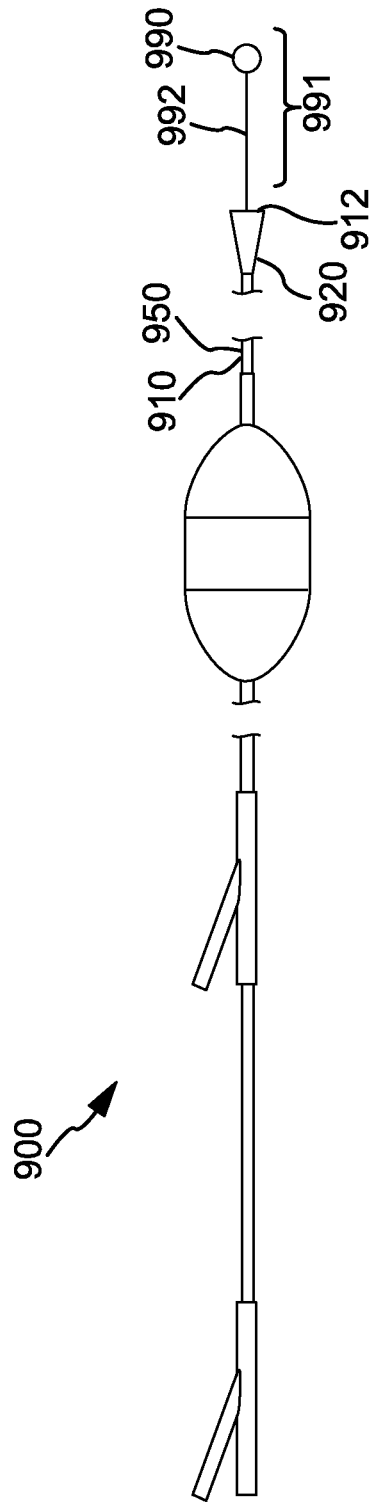
FIGS. 27-28 illustrate side views of a flow-reversal catheter device comprising a third occluder.

When a treatment site is in the location of a vessel bifurcation, such as the common carotid artery bifurcation, flow-reversal can be enhanced by occluding the main vessel as well as the branch vessel not being treated. This will further ensure that blood flow when reversed will flow into the conduit rather than flowing into the branch vessel. For example, with reference to FIGS. 27-28, flow-reversal catheter device 900 can comprise a third occluder 990. In the case of treating a lesion in the internal carotid artery, the common carotid artery will be occluded with first occluder 920 and the external carotid artery can be occluded by third occluder 990.

Similar to a first and second occluder, third occluder 990 comprises any radially expandable and collapsible structure and is configured to substantially block the flow of blood through a vessel when in an expanded state. Third occluder 990 is delivered in a collapsed configuration and then expanded to block the flow of blood in a branch vessel, such as the external carotid artery (ECA), as illustrated in FIG. 19. Third occluder 990 can comprise an inflatable occluder or a slide-actuated occluder as described above.

Figure 28:
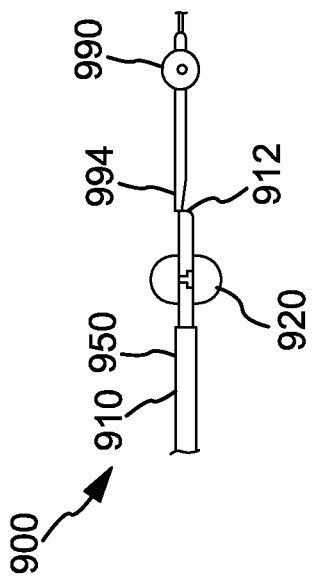

With reference to FIG. 28, third occluder 990 can comprise a balloon wire 991, which is deliverable through catheter 910 to occlude a branch vessel. Balloon wire 991 comprises an elongate member 992, such as a hypotube, with an expandable and collapsible occluder coupled to the distal region thereof. Elongate member can comprise a lumen to inflate and deflate an inflatable occluder or be configured to actuate slideably a slide-actuated occluder into expanded or collapsed configurations. Alternatively, with reference to FIG. 27, catheter 910 can comprise a distally projecting strut 994 having a third occluder 990, which is configured so that blood can still flow into distal opening 912 of catheter 910 and into conduit 950.

Flow-reversal catheter device can be configured so that the distance between first, second, and/or third occluders, when present, is adjustable. For example, first, second, and/or third occluders can be telescopic relative to each other such that the catheter(s) or elongate member(s) to which each is coupled is slideably coupled to the other catheter(s) or elongate member(s). Furthermore, first, second, and/or third occluders can comprise a radio-opaque marker to facilitate locating the occluder in situ.

Similarly, first, second, and/or third occluders, when present, can be configured for adjustable attachment to the catheter body. The first occluder and/or the second occluder can be configured for adjustable attachment on a catheter or an introducer sheath. Adjustable attachment includes the ability of the user to move an occluder along a catheter and attach at a desired location on the catheter. This can include the ability to disengage attachment and reengage attachment.

The respective size of each occluder is sufficient to occlude the targeted vessel. For example, in an embodiment, the first occluder can occlude the common carotid artery and can be sized as such. The second occluder can occlude the descending thoracic aorta, common iliac artery, or the abdominal aorta and can be sized as such. The third occluder can occlude a branch vessel such as the internal or external carotid artery and can be sized as such.

A catheter device can further comprise a therapeutic agent, such as heparin. For example, heparin can be imbibed on inner surface of a catheter or on a filter to prevent or minimize any clotting as blood travels through device toward the return port.

A method for reversing blood flow in a vessel, such as an artery supplying blood to the brain—utilizing a flow-reversal catheter device as described herein comprising a second occluder—can comprise the steps of locating a first occluder in an artery supplying blood to the brain; locating a second occluder in an artery so as to lower the pressure at a return port upon expansion of the second occluder, e.g., such location can be downstream of the left common carotid artery; and expanding the first and second occluders whereby blood flows through the conduit from a distal end of the catheter to the return port. The method can further comprise the step of filtering blood from the conduit to remove embolic debris therein. The second occluder can be substituted for or augmented with another mechanism configured to create a pressure gradient. If, instead of flowing through the conduit, the reversed blood flow is flowing into a branch vessel, a third occluder can be deployed distal the first occluder within the branch vessel to occlude the branch vessel.

Methods for treatment of a cerebral vessel having a stenosis utilizing the flow-reversal catheter device are described. The lumen of the cerebral vessel is accessed in one of three ways, depending on the location of the stenosis. Lesions in the distal posterior circulation would be approached by a cut down to the vertebral artery. Lesions in the distal anterior circulation would be approached percutaneously through the common carotid arteries. Proximal lesions in all vessels would be approached percutaneously through the femoral artery. In each case, after vasculature is accessed, a conventional guidewire is passed within the lumen of the cerebral vessel. Next, the distal end of the catheter is introduced over the guidewire into the cerebral vessel stopping proximal to the lesion. The first occluder is inflated until the vessel is occluded. This can be determined by fluoroscopic visualization of the stagnant flow or by gentle traction on the catheter. Once reverse flow is confirmed, the interventional component can be inserted through the lumen and the lesion treated. Retrograde blood flow will flush blood and debris through the conduit and to the filter, if present, and then returned via the blood return port. Finally, the interventional device and then the catheter device are removed.

These methods of using the catheter device disclosed herein serve as examples and are not limiting. Further uses will be recognized by a skilled artisan. For example, the creation of a low-pressure site through arterial restriction can be anywhere along the path of the catheter body, e.g., aorta, iliac, or femoral sites can be used.

EXAMPLE

By way of example, one embodiment of a catheter system can be made and used as follows.

A first occluder and a catheter are commercially available from Gore's Flow Reversal System. The catheter can be 6 Fr. stent delivery compatible with approximately a 0.120" OD and approximately 93 cm working length. The first occluder can comprise a compliant balloon for occlusion of vessels from about 5 to about 12 mm. An external filter set supplied with Gore's Flow Reversal System can also be utilized as additional conduit to filter embolic debris from rerouted blood.

A second occluder and a second occluder catheter, which fit over the above-described catheter, can comprise an outer tube slideably coupled over an inner tube with a compliant balloon attached to the outer tube, which is inflated via an inflation lumen residing in between the inner tube and the outer tube. The inner tube slidably fits over the catheter and can have an inner diameter of 0.125", an outer diameter of 0.140" and a length of 47 cm. The inner tube can be made of Pebax 7233. The outer tube has a sufficient annular space to slide over the inner tube to form an inflation lumen therebetween. For example, the outer tube can have an inner diameter of 0.150", an outer diameter of 0.166" and a length of 41 cm (body stock) plus 1.5 cm (tip material). The outer tube can also be made of Pebax 7233. The compliant balloon is commercially available from Advanced Polymers Inc. (API #30000000JA) and made from urethane having low durometer. The dimension of the compliant balloon can comprise a 28 mm diameter, a 30 mm length, and a neck inner diameter of approximately 0.150", with the ability to be stretched over the 0.166" outer tube. The second catheter is connected to a hub, which is commercially available from Qosina, and has a polycarbonate Y-arm (both female luer connections) drilled thru with a 0.145" and tip drilled to 0.170". In order to bond second catheter to hub and to assemble second occluder/second occluder catheter, a UV cure adhesive can be used, such as Dymax 208 CTH, commercially available from DYMAX Corporation, Torrington, Conn. Stepwise instructions for the assembly are provided below.

An introducer sheath, which fits over second catheter, is commercially available from COOK having a 14 Fr. sheath size, 20 cm total length, and a side port for flushing (flexible extension).

Third Occluder, which is deliverable through the lumen of the catheter, can comprise the external carotid occlusion balloon wire supplied with Gore's Flow Reversal system.

A secondary endovascular device, which is deliverable through the lumen of the catheter to the treatment site, can comprise a carotid stent. In order to assemble the second occluder/second occluder catheter, the first step is to trim both necks of compliant balloon to approximately 1 cm in length. Next, position outer tube (body stock) over an approximately 0.148", Polytetrafluoroethylene (PTFE) coated stainless steel mandrel. Once in position, place a few drops of Dymax 208CTH around the circumference of distal end of the outer tube, and slide the proximal neck of the compliant balloon over the outer tube to provide for approximately a 1 cm bond length. Wipe off excess adhesive, and UV cure for approximately 15 seconds. To connect the distal neck of the balloon to the outer tube, place a few drops of Dymax 208CTH around the circumference of the proximal end of the outer tube (tip section), and slide the distal neck of the compliant balloon over the proximal end of the tip section of the outer tube to provide approximately 1 cm of bonding area and approximately 1 cm for tip forming. Again, wipe off excess adhesive, and UV cure for approximately 15 seconds. Once cured, remove the outer tube and compliant balloon assembly from mandrel. In order to connect to this assembly to the inner tube, place the inner tube on an approximately 0.122" PTFE coated stainless steel mandrel, and slide the inner tube through the outer tube plus balloon, aligning the end of the inner tube with the distal end of the outer tip tubing. Once in position, apply Dymax 208CTH into the annular space of tip (gap between inner tube and outer tip section) and UV cure for approximately 15 seconds. This should successfully seal off the annular space from any leak paths. Once cured, trim proximal end of assembly so that inner tube sticks out of outer tube by approximately 2.5 cm. Prepare a polycarbonate y-arm from Qosina with a large enough size to accommodate the second catheter by first drilling out the main lumen of the hub to accommodate the inner tubing (~0.145"). Then, drill out distal end of y-arm to accommodate the outer tubing up to inflation port (0.170" drill, 1 cm deep). When drilling is complete, position hub over the proximal end of the assembly and glue with Dymax 208CTH. UV cure for approximately 15 sec per glue location, and remove from the mandrel.

In order to use the above-described embodiment of the catheter system, prepare the first occluder and the catheter; the second occluder and the second occluder catheter; and the introducer sheath in accordance with any supplied instructions for use, which includes flushing all catheters with saline to remove air prior to use. Once prep work is complete, access to the patient's femoral artery is established with the 14 Fr. introducer sheath. The second occluder catheter is then slid through the lumen of introducer sheath so that the second occluder is in a suitable location, such as the iliac or aorta. Next, the catheter is passed thru the lumen of second occluder catheter and the first occluder is positioned in the Common Carotid Artery (CCA). Once occluder positions are set, the external filter set is connected to the blood exit port of the catheter and to the side port of the introducer sheath. A 3-way valve can be utilized, if needed. Next, the third occluder is guided thru the main lumen of the catheter to a suitable location in the External Carotid Artery (ECA) followed by the secondary endovascular device, e.g., stent, to be staged proximal the location to be treated.

From here, the occluders are inflated. First, the third occluder of the external balloon wire is inflated in the ECA, and then the first occluder in the CCA. Inflate the second occluder in the appropriate location, iliac or aorta as noted above. If necessary, the second occluder can be repositioned by sliding second occluder catheter along catheter such as to prevent occlusion of critical arteries (e.g., renal arteries). Once all occluders are inflated, the clinician will ensure blood is flowing out of the exit port from the catheter, through the external filter set, and returning to the patient's arterial side via the side port of the introducer sheath.

Once reverse flow is established, the Carotid Artery procedure, utilizing the secondary endovascular device, is performed. When no further manipulations are needed about the treated lesion, the main conduit is aspirated. The filter can be inspected for embolic debris at this point or at any other point during the procedure. The occluders are then deflated, and the catheter system is removed.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A method for providing embolic protection comprising the steps of providing a single access catheter device comprising:
   a catheter having a proximal and distal region with a lumen therethrough;
   a first occluder located within the distal region of the catheter;
   a second occluder located proximal to the first occluder;
   a return port located proximal to the second occluder; and
   a conduit connecting the distal the end of catheter to the return port;
   locating the first occluder in a vessel proximate to a treatment site;
   locating the second occluder in an aorta downstream of a renal artery;
   expanding the first occluder and the second occluder whereby blood flows through the conduit from a distal end of the catheter to the return port.

2. The method of claim 1, wherein the conduit comprises the lumen of the catheter and the interstitial space between an introducer sheath and the catheter.

3. The method of claim 1, further comprising the step of filtering the blood flowing through the conduit to remove at least a portion of embolic debris therein.

4. The method of claim 1, wherein the vessel is a cerebral vessel.

5. The method of claim 1, further comprising the step of expanding a third occluder distal to the first occluder to occlude a branch vessel.

6. The method of claim 5, wherein the branch vessel is the external carotid artery.

7. The method of claim 1, further comprising the step of delivering a medical device through the lumen to the treatment site.

8. The method of claim 7, wherein the medical device comprises a stent.

* * * * *